United States Patent [19]

Teramae et al.

[11] Patent Number: 5,693,644
[45] Date of Patent: Dec. 2, 1997

[54] WOOD PRESERVATIVES

[75] Inventors: Tomohiro Teramae, Toyonaka; Tsuguhiro Katoh, Sanda, both of Japan

[73] Assignee: Sumitomo Chemical Company, Limited, Osaka, Japan

[21] Appl. No.: 516,401

[22] Filed: Aug. 17, 1995

[30] Foreign Application Priority Data

Aug. 29, 1994 [JP] Japan .................................. 06-203488

[51] Int. Cl.$^6$ ...................................... A01N 43/54
[52] U.S. Cl. .................................. 514/269; 514/256
[58] Field of Search ........................ 514/256, 269

[56] References Cited

U.S. PATENT DOCUMENTS 4,783,466  11/1988  Katoh et al. .................. 514/256
5,223,524  6/1993  Valcke ............................ 514/383

OTHER PUBLICATIONS

Mizuguchi et al, E. A., vol. 118, (1993) 118: 1858305.

*Primary Examiner*—Allen J. Robinson
*Attorney, Agent, or Firm*—Sughrue, Mion, Zinn, Macpeak & Seas, PLLC

[57] ABSTRACT

A wood preservative comprising a pyridylpyrimidine compound of the formula [I]

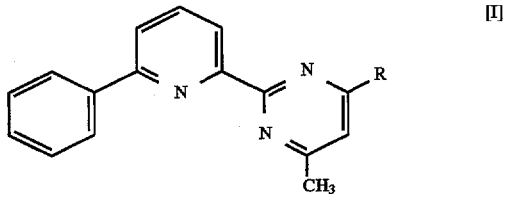

wherein R represents a hydrogen atom, a lower alkyl group, a lower alkoxy group as an active ingredient, which has a high wood-preserving efficacy.

6 Claims, No Drawings

WOOD PRESERVATIVES

The present invention relates to a wood preservative and a method for preserving wood using the same.

Wood is usually exposed to severe conditions outdoors such as the direct rays of the sun and rain over a long term. Generally, chemicals such as fungicides for agriculture easily decompose and hardly remain in soils or the like over a long term, so that it is difficult to have a wood-preserving efficacy which is practically useful using said chemicals.

The present inventors have made extensive research on developing a practical wood preservative whose wood-preserving efficacy is superior to that of conventional wood preservatives, and as a result, they have found a compound capable of achieving the purpose.

According to the present invention, there is provided a wood preservative comprising a pyridylpyrimidine compound of the formula [I]

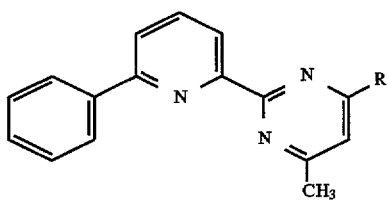

[wherein R represents a hydrogen atom, a lower alkyl group (e.g. $C_{1-4}$ alkyl group) or a lower alkoxy group (e.g. $C_{1-4}$ alkoxy group)] as an active ingredient and a method for preserving wood using a fungicidally effective amount of the same.

Examples of the compound [I] are listed below,
(1) 4-methyl-2-(6-phenylpyridin-2-yl)pyrimidine
(2) 4,6-dimethyl-2-(6-phenylpyridin-2-yl)pyrimidine
(3) 4-methoxy-6-methyl-2-(6-phenylpyridin-2-yl)-pyrimidine Compound [I] can be produced according to the method described in the specification of U.S. Pat. No. 4,783,466.

In the application of the present wood preservative, compound [I] may be used as it is without adding any other ingredient. However, compound [I] is usually mixed with an inert carrier such as a solid carrier, a liquid carrier or a gaseous carrier and, if necessary, a surface active agent, a stabilizer and other auxiliaries for formulation are added to the mixture, after which the resulting mixture is formulated into an oil formulation; an emulsifiable concentrate; a wettable powder; a flowable formulation such as an in-water suspension, an in-water emulsion, etc.; a dust; an aerosol; or the like. The formulation thus obtained is used.

These formulations contain compound [I] as an active ingredient in an amount of usually 0.01 to 95% by weight, preferably 0.2 to 60% by weight.

The solid carrier used in the formulation includes, for example, fine powders and granules of clays (kaolin clay, diatomaceous earth, synthetic hydrated silicon dioxide, bentonite, fubasamiclay, terra alba, etc.), talcs, quartz, sericite, calcium carbonate, other inorganic minerals, activated charcoal, sulfur, ceramics, hydrated silica and the like. The liquid carrier includes, for example, alcohols [ethanol, isopropyl alcohol, 3-methyl-3-methoxybutanol, glycols (polyethylene glycol, polypropylene glycol, etc.), etc.], ketones (acetone, methyl ethyl ketone, etc.), aromatic hydrocarbons [alkylbenzene (toluene, xylene, etc.), methylnaphthalene, etc.], non-aromatic hydrocarbons (hexane, cyclohexane, kerosene, light oil, etc.), esters (ethyl acetate, butyl acetate, isopropyl myristate, 3-methyl-3-methoxybutyl acetate, etc.), nitriles (acetonitrile, isobutyronitrile, etc.), ethers (diisopropyl ether, dioxane, etc.), acid amides (N,N-dimethylformamide, N,N-dimethylacetamide, etc.), halogenated hydrocarbons (dichloromethane, trichloroethane, etc.), vegetable oils (soybean oil, cottonseed oil, etc.), dimethylsulfoxide, water and the mixture thereof. The gaseous carrier, namely, propellant, include, for example, chlorofluorocarbons, butane, LPG (liquefied petroleum gas), dimethyl ether, carbon dioxide, etc.

The surface active agent includes, for example, alkylsulfuric esters, alkylsulfonic acid salts and alkylarylsulfonic acid salts, alkyl aryl ethers and polyoxyethylenated products thereof, polyethylene glycol ethers, polyhydric alcohol esters, sugar alcohol derivatives, etc.

The auxiliaries for formulation are a sticking agent, a dispersing agent, etc. and include, for example, polysaccharides (starch, gum arabic, cellulose derivatives, alginic acid, etc.), synthetic water-soluble polymers (polvinyl alcohol, polyvinyl pyrrolidone, polyacrylic acids, etc.), casein, gelatin, lignin derivatives, bentonite, sugars, and the stabilizer includes, for example, PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), a vegetable oil, a mineral oil, a fatty acid and its ester, etc.

The flowable formulation is generally obtained by microdispersing 1 to 75% by weight of compound [I] in water containing 0.5 to 15% by weight of a dispersing agent, 0.1 to 10% by weight of a suspension adjuvant (for example, a protective colloid and a thixotropy-imparting compound), and optionally adequate auxiliaries such as an antifoaming agent, a rust inhibitor, a stabilizer, a spreader, a penetrant auxiliary and an antifreezing agent. Compound [I] can also be formulated into an in-oil suspension by using, instead of water, an oil in which compound [I] scarcely dissolves. As the protective colloid, there is used, for example, gelatin, casein, gums, cellulose ether, polyvinylalcohol or the like. As the thixotropy-imparting compound, there is used, for example, bentonite, aluminium magnesium silicate, xanthane gum, polyacrylic acid, or the like.

The formulations thus obtained are used as they are or after diluting them with water, etc.

The oil formulation, dust, granule and aerosol are applied as they are and the emulsifiable concentrate, wettable powder and flowable formulation are applied after diluting them with water to make the concentration of compound [I] 0.01 to 10% by weight, preferably 0.05 to by weight.

The amount and concentration of the active ingredient applied are varied depending on the kind of formulation, the application timing, the application place, the application method, the kind of wood rotting fungi and the degree of wooden damage, etc. and they can be increased or decreased regardless of the above range.

The amount of compound [I] applied is generally 0.1 to 10 g per m² of surface area of wood.

The present wood preservative is applied to wood by a surface treatment means such as dipping, spraying, coating, etc., or a means such as injection under pressure or injection under vacuum, or applied in admixture with an adhesive (for example, phenol resin, melamine resin, urea resin) for plywood to prepare a plywood or especially applied to construction materials, to act as a controlling agent for wood rotting fungi.

The present wood preservative is used preferably as a wooden surface treating agent and, in this case, usually used in the form of an oil formulation.

The oil formulation generally contains compound [I] in an amount of 0.01 to 5% by weight and usually applied in an amount of 50 to 200 g per m² of surface area of wood.

The present wood preservative can be applied in admixture with or separately from and simultaneously with other wood preservatives, insecticides, acaricides, termiticides (controlling agents for termites), fungicides or synergists.

The termiticides to be used include chlorpyrifos, phoxim, fenitrothion, fenobucarb, permethrin, tralomethrin, cypermethrin, deltamethrin, cyfluthrin and fenvalerate.

The wood rotting fungi that can be controlled by the present wood preservative, are for example, *Coriolus versicolor, Tyromyces palustris, Serpula lacrymans,* etc. and the wood that is the object for controlling wood rotting fungi includes, for example, Fagaceae such as Japanese beech, Taxodiaceae such as Japanese cedar, Pinaceae such as Japanese red pine and the like.

The present application relies for priority upon the inventors' Japanese Patent Application No. 06/203488 filed Aug. 29, 1994, the content of which is herein incorporated by reference.

The present invention is specifically explained below referring to Examples. In the Examples, parts are by weight unless otherwise specified, and the compounds are represented as the compound number shown above.

FORMULATION EXAMPLE 1

With 1 part of compound (1), (2) or (3) were mixed 0.2 part of permethrin (controlling agent for termite), 1.5 parts of bis(2,3,3,3-tetrachloropropyl) ether (synergist), 10 parts of 3-methyl-3-methoxybutanol and 87.3 parts of kerosene to prepare an oil formulation.

FORMULATION EXAMPLE 2

With 2 parts of compound (1), (2) or (3) were mixed 88 parts of xylene and 10 parts of Sorpol SM200 (surfactant manufactured by Toho Chemical Co., Ltd.) to prepare an emulsifiable concentrate.

TEST EXAMPLE 1

A wooden piece (20 mm×20 mm×0.5 mm, the surface of 20 mm×20 mm was of straight grain) of Japanese beech was dipped in the oil formulation prepared in Formulation Example 1 for 20 seconds, and thereafter air-dried for 2 days to prepare a test specimen. The test specimen was dried at 60°±2° C. for 48 hours, after which the weight ($W_1$) of the test specimen was measured. The test specimen was sterilized and placed in a plate in which *Coriolus versicolor* was being cultured, and then, cultivation was effected at 26°±2° C. at a humidity of 80% for 2 weeks. After the cultivation for 2 weeks, the test specimen was taken out of the plate and the mycelia and other extraneous matters were removed therefrom, after which the test specimen was dried at 60°±2° C. for 48 hours. Thereafter, the weight ($W_2$) of the test specimen was measured.

The weight reduction percentage (%) was calculated according to the following equation:

$$\text{Weight reduction percentage } (\%) = W_1 - W_2 / W_1 \times 100$$

As a result, all of compound (1), compound (2) and compound (3) showed a good result of the weight reduction percentage of 3% or less.

Next, it is shown that controlling effects of the present composition on wood rotting fungi are very practical according to the test method provided by Japan Wood Preservation Association.

TEST EXAMPLE 2

Cut end surfaces of a wooden piece of Japanese beech (40 mm×20 mm×5 mm, the surface of 40 mm×20 mm was of straight grain) were sealed with an epoxy resin and the wooden piece was dipped in the oil formulation of compound (2) prepared in Formulation Example 1 (110±10g/m$^2$), and thereafter air-dried for 20 days to prepare a test specimen. The test specimen was dipped in water [water:test specimen=10:1 (volume ratio)] at 25°±3° C. for 5 hours, and then the specimen was dried at 40°±2° C. for 19 hours. This dipping and drying operation was repeated 30 times. The test specimen after the operation was dried at 60°±2° C. for 48 hours and then placed in a desiccator for 30 minutes, after which the weight ($W_1$) of the test specimen was measured. The test specimen was sterilized and placed in a culture vial in which *Coriolus versicolor* was being cultured, and then cultivation was effected at 26°±2° C. at a humidity of 80% for 8 weeks. After the cultivation for 8 weeks, the test specimen was taken out of the culture vial and the mycelia and other extraneous matters were removed therefrom, after which the test specimen was dried at 60°±2° C. for 48 hours and then placed in a desiccator for 30 minutes, after which the weight ($W_2$) of the test specimen was measured.

Furthermore, the same test as above was repeated except that *Tyromyces palustris* and a wooden piece of Japanese cedar were used instead of *Coriolus versicolor* and a wooden piece of Japanese beech, respectively.

The weight reduction percentage (%) was calculated according to the equation of Test Example 1.

As a result, both of Japanese beech and Japanese cedar showed a good result of the weight reduction percentage of 3% or less (which passes the test method provided by Japan Wood Preservation. Association).

What is claimed is:

1. A method for controlling wood rotting fungi comprising applying to wood a fungicidally effective amount of a composition comprising a pyridylpyrimidine compound of the formula [I]

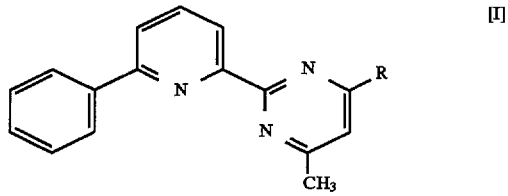

wherein R represents a hydrogen atom, a lower alkyl group or a lower alkoxy group, as an active ingredient and an inert carrier, and wherein the rotting fungi is at least one fungus selected from the group consisting of *Coriolus versicolor, Tyromyces palustris* and *Serpula lacrymans*.

2. A method for preserving wood comprising applying to wood a fungicidally effective amount of a wood preservative comprising a pyridylpyrimidine compound of the formula [I]

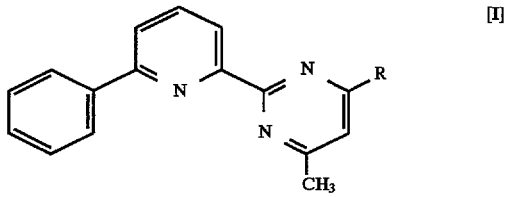

wherein R represents a hydrogen atom, a lower alkyl group or a lower alkoxy group, as an active ingredient and an inert carrier.

3. The method for preserving wood according to claim 2, wherein R represents a hydrogen atom, a methyl group or a methoxy group.

4. The method for preserving wood according to claim 2, wherein the wood preservative is applied to a wooden surface.

5. The method for preserving wood according to any one of claims 2 to 4, wherein the wood preservative is in the form of an oil formulation.

6. The method for preserving wood according to claim 5, wherein the wood preservative is applied to wood in an amount of 50 to 200 g of the oil formulation per m$^2$ of surface area of wood and in an amount of 0.1 to 10 g of the active ingredient per m$^2$ of surface area of wood.

* * * * *